(12) United States Patent
Shires

(10) Patent No.: US 6,573,987 B2
(45) Date of Patent: Jun. 3, 2003

(54) LCC DEVICE INSPECTION MODULE

(75) Inventor: Mark R. Shires, Glendale, WI (US)

(73) Assignee: Robotic Vision Systems, Inc., Canton, MA (US)

( * ) Notice: Subject to any disclaimer, the term of this patent is extended or adjusted under 35 U.S.C. 154(b) by 0 days.

(21) Appl. No.: 10/039,378

(22) Filed: Jan. 2, 2002

(65) Prior Publication Data

US 2002/0085199 A1 Jul. 4, 2002

Related U.S. Application Data

(60) Provisional application No. 60/259,297, filed on Jan. 2, 2001.

(51) Int. Cl.[7] ............................. G01N 21/00; H04N 7/18
(52) U.S. Cl. .................................. 356/237.2; 348/126
(58) Field of Search ......................... 356/237.1, 237.2, 356/237.3; 250/559.46; 348/336, 337, 338, 339, 126; 382/146

(56) References Cited

U.S. PATENT DOCUMENTS

| | | | | | |
|---|---|---|---|---|---|
| 3,922,069 | A | * | 11/1975 | Kishikawa et al. | 359/633 |
| 4,873,569 | A | * | 10/1989 | Hirosawa | 348/338 |
| 5,140,643 | A | * | 8/1992 | Izumi et al. | 382/153 |
| 5,276,546 | A | * | 1/1994 | Palm et al. | 348/126 |
| 5,452,080 | A | * | 9/1995 | Tomiya | 356/237.1 |
| 5,909,285 | A | * | 6/1999 | Beaty et al. | 356/237.1 |
| 5,995,220 | A | * | 11/1999 | Suzuki | 348/126 |
| 6,055,055 | A | * | 8/2000 | Toh | 356/237.2 |
| 6,116,739 | A | * | 9/2000 | Ishihara et al. | 353/31 |
| 6,128,034 | A | * | 10/2000 | Harris et al. | 348/126 |
| 6,211,955 | B1 | * | 4/2001 | Basiji et al. | 356/326 |
| 6,292,261 | B1 | * | 8/2001 | Fihbaine et al. | 348/126 |
| 6,359,694 | B1 | * | 3/2002 | Stredele et al. | 356/237.1 |

* cited by examiner

Primary Examiner—Zandra V Smith
(74) Attorney, Agent, or Firm—Michael Best & Friedrich LLP

(57) ABSTRACT

An LCC inspecting device includes a mirror having non-parallel front and rear surfaces, and reflective coatings on the front and rear surfaces. The reflective coatings reflect light of frequencies different from each other such that light of a first frequency reflects off the front surface of the mirror and light of a second, different frequency reflects off the rear surface. The LCC device may therefore be inspected from different angles by selectively using light of the first and second frequencies.

10 Claims, 5 Drawing Sheets

LCC DEVICE INSPECTION MODULE

This application claims the benefit of Provisional application Ser. No. 60/259,297, filed Jan. 2, 2001.

BACKGROUND OF THE INVENTION

The invention relates to machine vision systems and more particularly to a machine vision system adapted to inspect leadless chip carrier ("LCC") devices for quality control purposes.

It is known to inspect various types of electronic devices with machine vision systems. Most of these electronic devices are of the type having leads extending from the main body of the device. Known methods and apparatus for inspecting these types of devices include backlighting the device to display the device in silhouette such that the length and orientation of the leads is easily inspected with a camera.

Electronic semiconductor devices are typically visually inspected by machine vision systems as a form of quality control. LCC devices are different from electronic devices having leads. LCC devices include pads which are typically made of copper, and which are arranged around the periphery of an LCC device but do not extend significantly from the main body of the LCC device. Because of the nature of the pads and other aspects of LCC devices, the LCC devices can require the following inspections: copper smear (copper accidentally smeared between multiple pads of the device while sawing them apart), package warpage, pad standoff (3D pad-to-package measurement), package flaws, 2D pad measurement and integrity, and device orientation.

DETAILED DESCRIPTION OF THE INVENTION

Figure 2:
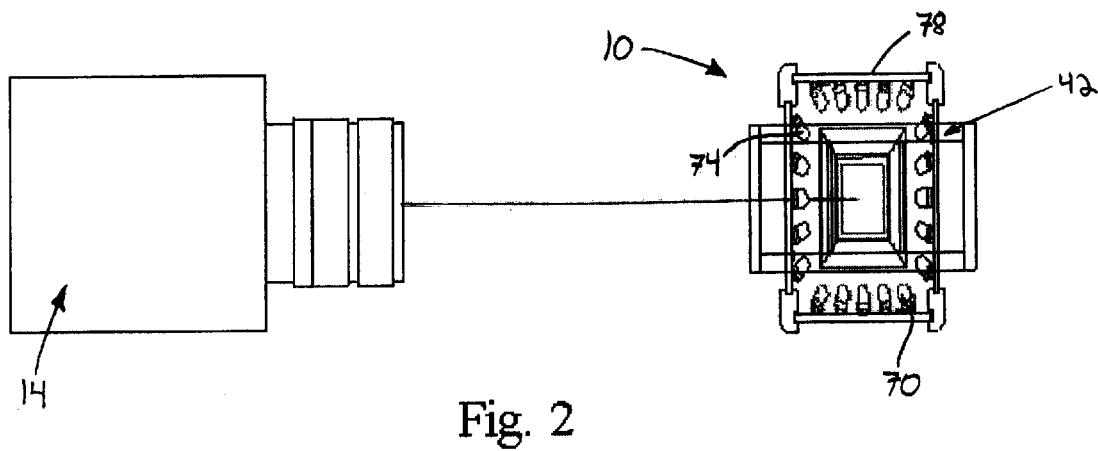
FIG. 2 is a top plan view of the module illustrated in FIG. 1.
Figure 3:
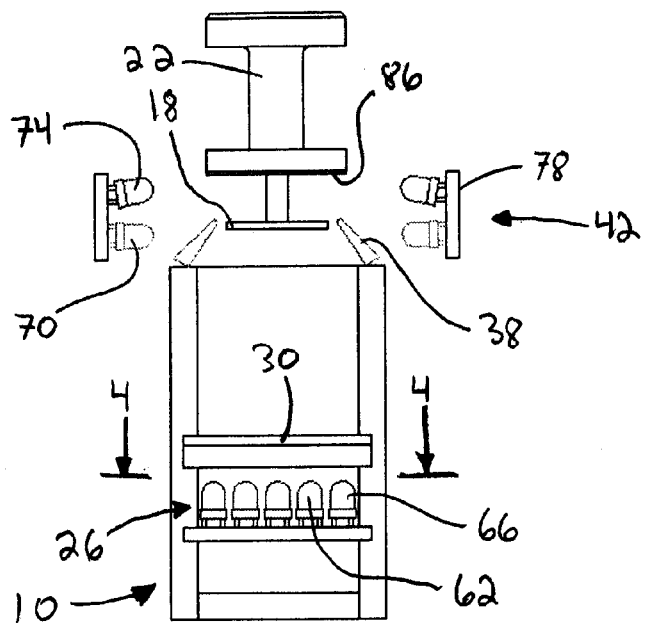
FIG. 3 is an end view of the module illustrated in FIG. 1.
Figure 4:
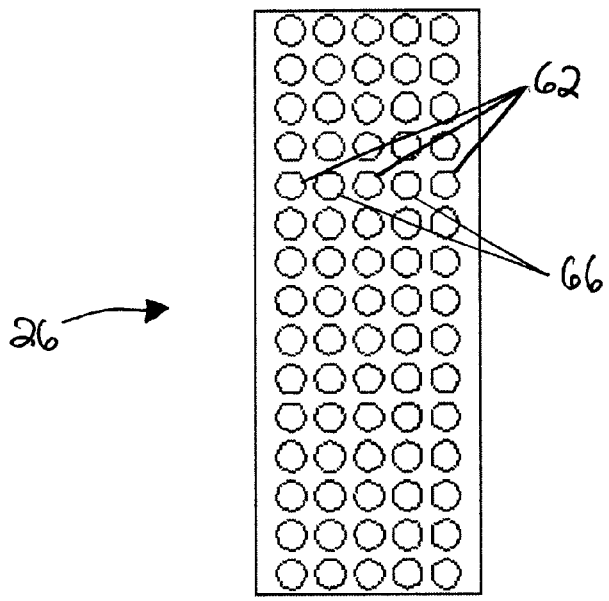
FIG. 4 is a view taken along line 4—4 in FIG. 3.

With reference to FIGS. 1–4, the present invention provides an LCC device inspection module 10 and a camera 14 used for viewing an LCC device 18 supported by a vacuum pick-and-place nozzle 22 in the inspection module 10. The inspection module 10 includes a lower bank of lights 26 arranged in a two-dimensional array as illustrated in FIG. 4, a white light diffuser 30, a beam splitter 34, four mirrors, beam splitters, or prisms 38 surrounding the LCC device 18, and an upper ring or bank of lights 42. By virtue of the beam splitter 34 and the mirrors 38, the camera 14 may view the bottom and all four sides of the LCC device 18 in a single image.

Figure 5:
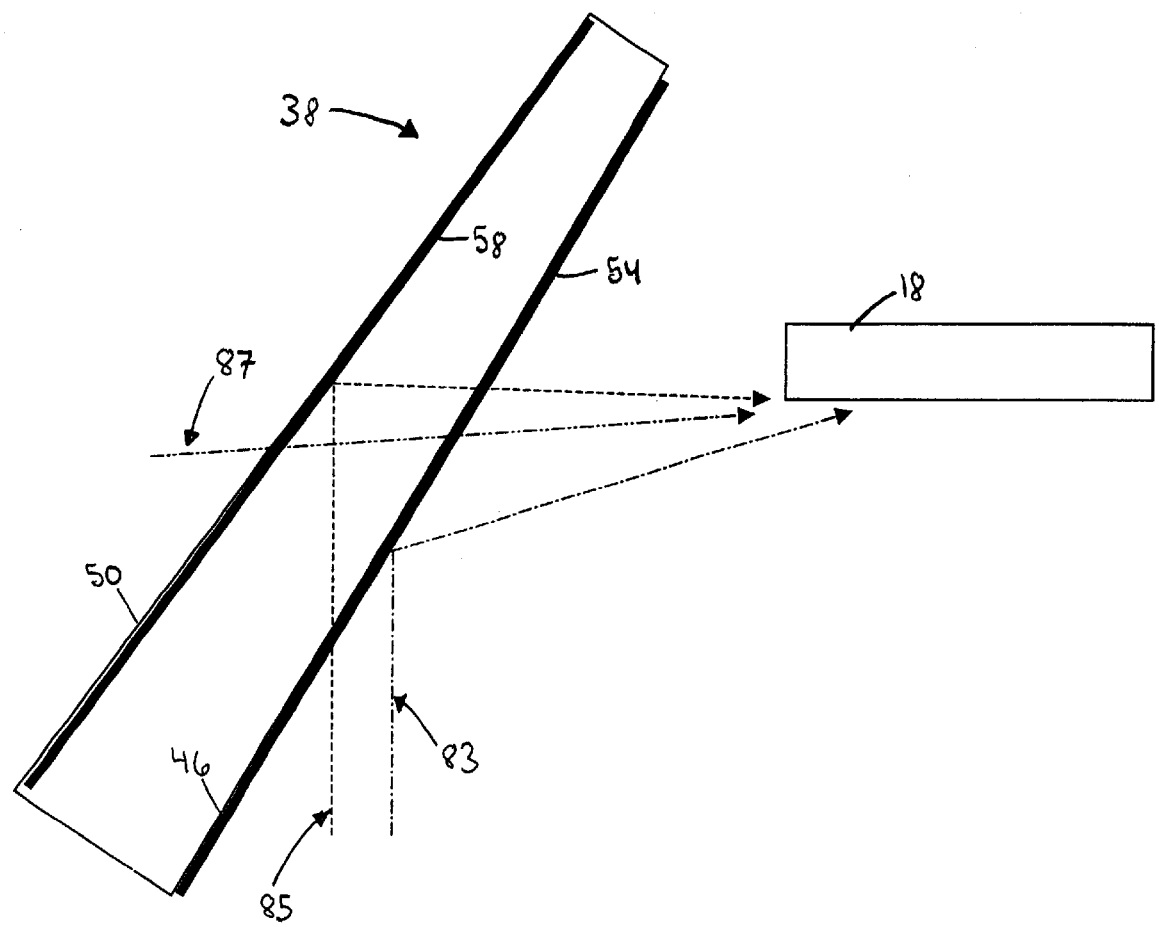
FIG. 5 is an enlarged view of a portion of the module illustrated in FIG. 1.

As seen in FIG. 5, each mirror 38 includes a front and a rear surface 46, 50. The front and rear surfaces 46, 50 are coated with reflective coatings 54, 58, respectively. The coating 54 on the front surface 46 is preferably dichroic or dichromatic (i.e., the coating 54 reflects only selected frequencies of light waves), and the coating 58 on the rear surface 50 may be broadband (i.e., reflects white light) or dichroic or dichromatic. The rear surfaces 50 of the mirrors 38 are non-parallel to the front surfaces 46. The reflective coatings 54, 58 permit one to select the perspective angle from which one desires to view the LCC device 18 by simply changing the wavelength of the illumination source. Several embodiments of the present invention are possible, and such embodiments may include different LED color combinations and different reflective coatings. Also, the LED's may be replaced with other light emitting elements, including fiber optic lights or any other suitable light source.

Figure 1:
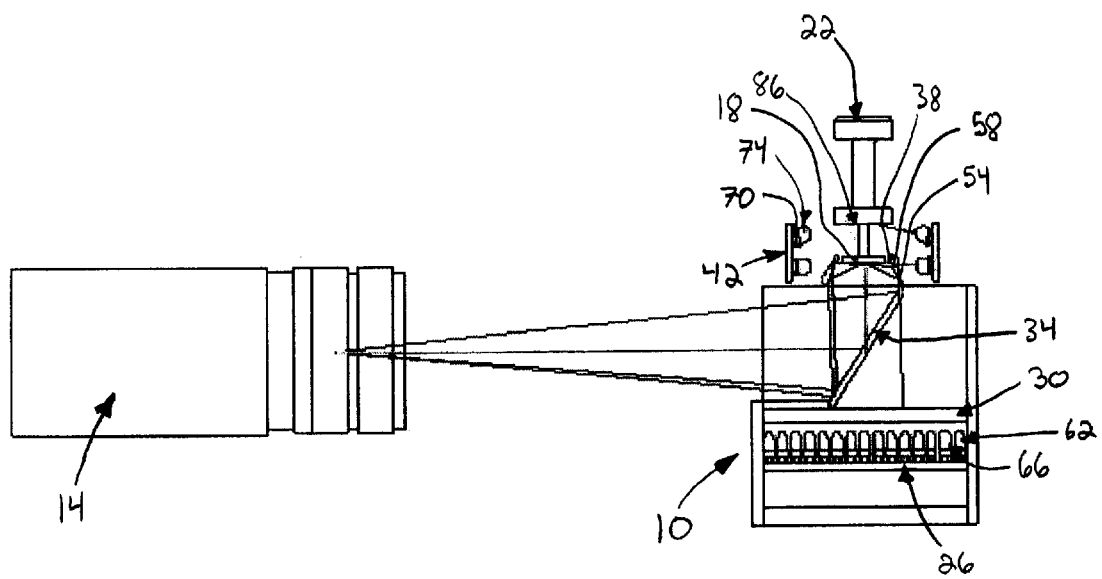
FIG. 1 is a side elevation view of an LCC device inspection module embodying the present invention.

With reference to FIGS. 1, 3, and 4, the lower bank of lights 26 preferably includes first and second sets of LED's 62, 66, respectively, having first and second frequencies (e.g., red and blue as illustrated), respectively. Preferably, the LED's are arranged in an alternating pattern between the first and second sets 62, 66 such that each LED of the first set 62 has an LED of the second set 66 on either side of it, and vice versa.

Turning to FIGS. 2 and 3, the upper ring of lights 42 is preferably comprised of third and fourth sets of LED's 70, 74 having third and fourth frequencies (e.g., green and blue as illustrated), respectively. The third and fourth sets of LED's 70, 74 are supported by a generally square or rectangular-shaped frame 78. The third set of LED's 70 are preferably supported on all four sides of the frame 78 and the fourth set of LED's 74 are preferably supported on just two sides of the frame 78. However, more or fewer LED's may be employed in each set 70, 74 and may be positioned differently around the frame 78 than illustrated (e.g., both sets 70, 74 may be positioned on all sides of the frame 78 or each set may be positioned on only two sides of the frame 78).

Operation of the module 10 will first be discussed with respect to detection of copper smear. Copper smear occurs in some instances when the LCC devices 18 are cut with a saw. If the cut is misaligned or otherwise not properly carried out, the copper of the pads 82 (see FIG. 6) may be heated and then smeared along an edge of the LCC device 18. Copper smear thus results in short circuiting of the LCC device 18. In order to inspect an LCC device 18 for copper smear, views of all four sides of the device 18 are needed. It is desirable to see the side and a little of the bottom of the LCC device 18 from each side view to completely inspect for the copper smear condition and verify that no electrical connection exists between the pads 82. Additionally, it is desirable that the LCC device 18 be viewed under more than a hemisphere of cloudy-day lighting illumination (explained in more detail below).

Figure 6:
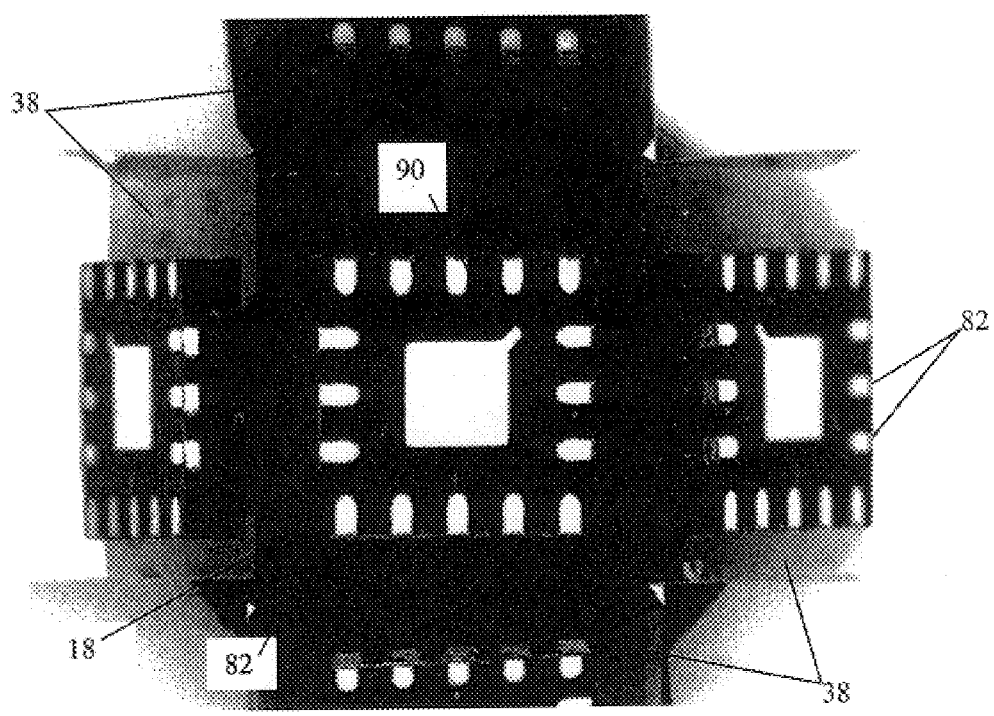
FIGS. 6 and 7 are views of LCC devices being inspected by the inspection module.
Figure 7:
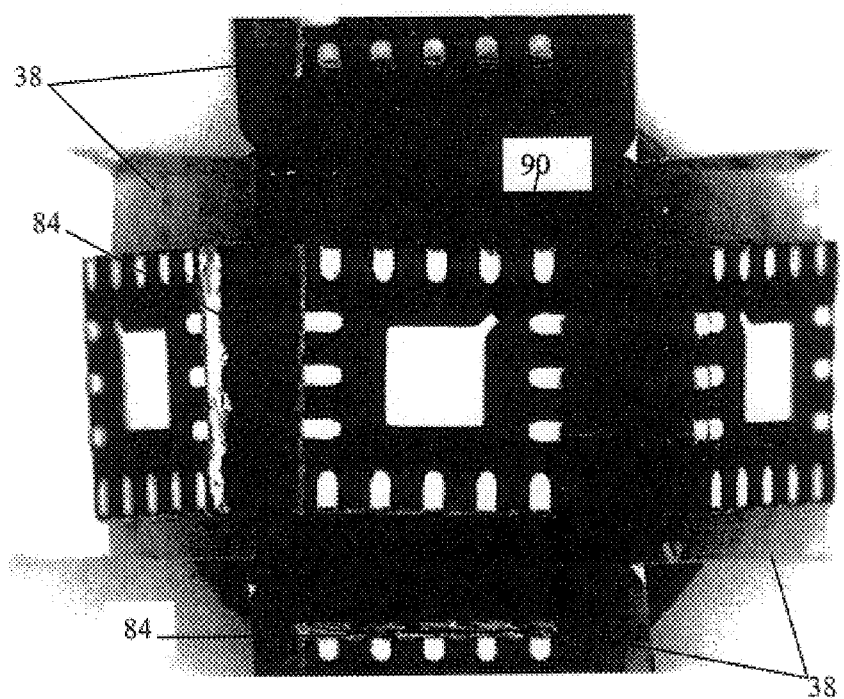

As seen in FIG. 5, the reflective coating 54 (e.g., a red reflective coating) on the front surfaces 46 of the mirrors 38 reflects light 83 of the frequency emitted by the first set of LED's 62 (e.g., red light). When the first set of LED's 62 is turned on, the light 83 emitted therefrom passes through the beam splitter 34, reflects off the LCC device 18, reflects off the coating 54 on the front surfaces 46 of the mirrors 38, then reflects off the beam splitter 34, and is received by the camera 14. The front surfaces 46 of the mirrors 38 are angled to provide the appropriate angle for inspecting copper smear on the LCC device 18 with the camera 14. FIGS. 6 and 7 illustrate LCC devices 18 as seen by the camera 14 with the first set of LED's 62 illuminated. FIG. 6 illustrates an LCC device 18 with acceptable pads 82, and FIG. 7 illustrates an LCC device 18 with unacceptable copper smear 84.

To inspect for warpage, one must view the edges of the LCC device 18 from the four side views, but at a slightly different angle than views necessary for copper smear inspection. More specifically, the warpage inspection requires profile (silhouette) views of the bottom edges and the pads 82 of the LCC device 18. Warpage inspection also requires an additional view of the device's edges (e.g., a bottom plan view), and often requires computer software to triangulate the two views.

Referring again to FIG. 5, the reflective coating 58 (e.g., a blue or broadband reflective coating) on the rear surfaces 50 of the mirrors 38 reflects light 85 of the frequency emitted by the second set of LED's 66 (e.g., blue light). When the second set of LED's 66 is illuminated, the light 85 will pass through the coating 54 on the front surfaces 46 of the mirrors 38 and be reflected off the coating 58 on the rear surfaces 50. The LCC device 18 will therefore be illuminated for the camera 14 from the angle of the rear surfaces 50 of the mirrors 38. From this perspective or angle, the bottom edges of the LCC device 18 are silhouetted for the camera 14.

An additional view of the device 18 is required to permit a final determination of warpage. In this regard, the fourth set of LED's 74 may be illuminated. The fourth set of LED's 74 is preferably angled toward the vacuum nozzle 22, a portion of which is coated with a diffusion layer 86 (FIGS. 1 and 3) for the fourth frequency of light (e.g., the diffusion layer may be a blue diffusion layer in the event the fourth set of LED's 74 emit blue light). The diffuse light reflected off the diffusion layer 86 backlights or silhouettes the LCC device 18 for the camera 14. The camera 14 can now see a silhouetted plan view of the bottom of the LCC device 18 reflected off the beam splitter 34. This provides the second view necessary for determining whether the LCC device 18 is warped.

The bottom plan view may also be used to inspect for 2D pad measurement and device orientation. With respect to 2D pad measurement, the inspection module 10 can determine the length and width of the pads 82 from the bottom plan view. With respect to device orientation, FIGS. 6 and 7 illustrate a lead-one indicator 90 included on each LCC device 18. The LCC device inspection module 10 can therefore determine the orientation of the first lead of the LCC device 18 and compare this with the desired orientation. In FIGS. 6 and 7, the lead-one indicator 90 points up and to the right. If the first lead is not in the proper position, the inspection module 10 sends signals upstream to a controller that manipulates the LCC device 18 into the proper orientation after it is passed out of the inspection module 10 and before it is packaged for shipment.

To inspect for pad 82 standoff and package flaws (e.g., cracks, pits, and/or protrusions) in the LCC device dark field illumination may be used. Alternatively, off-axis lighting (light rays hitting the device at an angle perpendicular to the axis of the camera) or low angle lighting may be used with similar results to dark field illumination.

Referring again to FIG. 5, such dark field illumination is provided by the third set of LED's 70, which is situated behind the mirrors 38. The light 87 emitted by the third set of LED's 70 is preferably of a different frequency (e.g., green light) as the light 83, 85 emitted by the first and second sets of LED's 62, 66. To enable dark field illumination, it is preferable that the reflective coating 58 on the rear surface 50 be non-reflective of the light 87 emitted by the third set of LED's 70 (e.g., the reflective coating 58 is preferably not a broadband reflector).

The light 87 from the third set of LED's 70 will therefore pass through the reflective coatings 54, 58 on the front and rear surfaces 46, 50 of the mirrors 38. Thus, a third picture of the device 18 may be taken with the device illuminated by the third set of LED's 70, and from an angle in which any surface defects of the LCC device 18 are visible. Illuminated by such dark filed illumination, the flat portion of the bottom surface of the device 18 appears to be a uniform color. Pits appear as dark areas having light peripheries, while protrusions appear as lighter colored areas on the bottom surface of the LCC device 18.

Some of the desired LCC device inspections are done with so-called "cloudy-day" illumination conditions. Cloudy-day lighting is a term used frequently within the machine vision community, and it refers to the type of lighting experienced on a cloudy or hazy day. This type of lighting requires diffuse light coming from a broad area. The breadth of the area from which the light is provided is commonly described in terms of a sphere or a portion of a sphere. It is often sufficient to use a hemisphere of diffuse light for machine vision applications. "Diffuse light" means that each point of the light source emits light in all directions. A piece of white plastic makes a good diffuser.

In the illustrated embodiment, the white diffuser 30 is a piece of white plastic, however, other materials may be used. The light emitted by the first and second sets of LED's 62, 66 evenly illuminates the white diffuser 30. Because the diffuse light is reflected off the mirrors 38, more than a hemisphere of diffuse illumination is created. Thus, the light from the first and second sets of LED's 62, 66 meets both the "diffuse" and "broad area" requirements for creating a cloudy-day lighting condition. If the body of the part is white, polarized light may achieve the permitted contrast to see copper smear.

Figure 8:
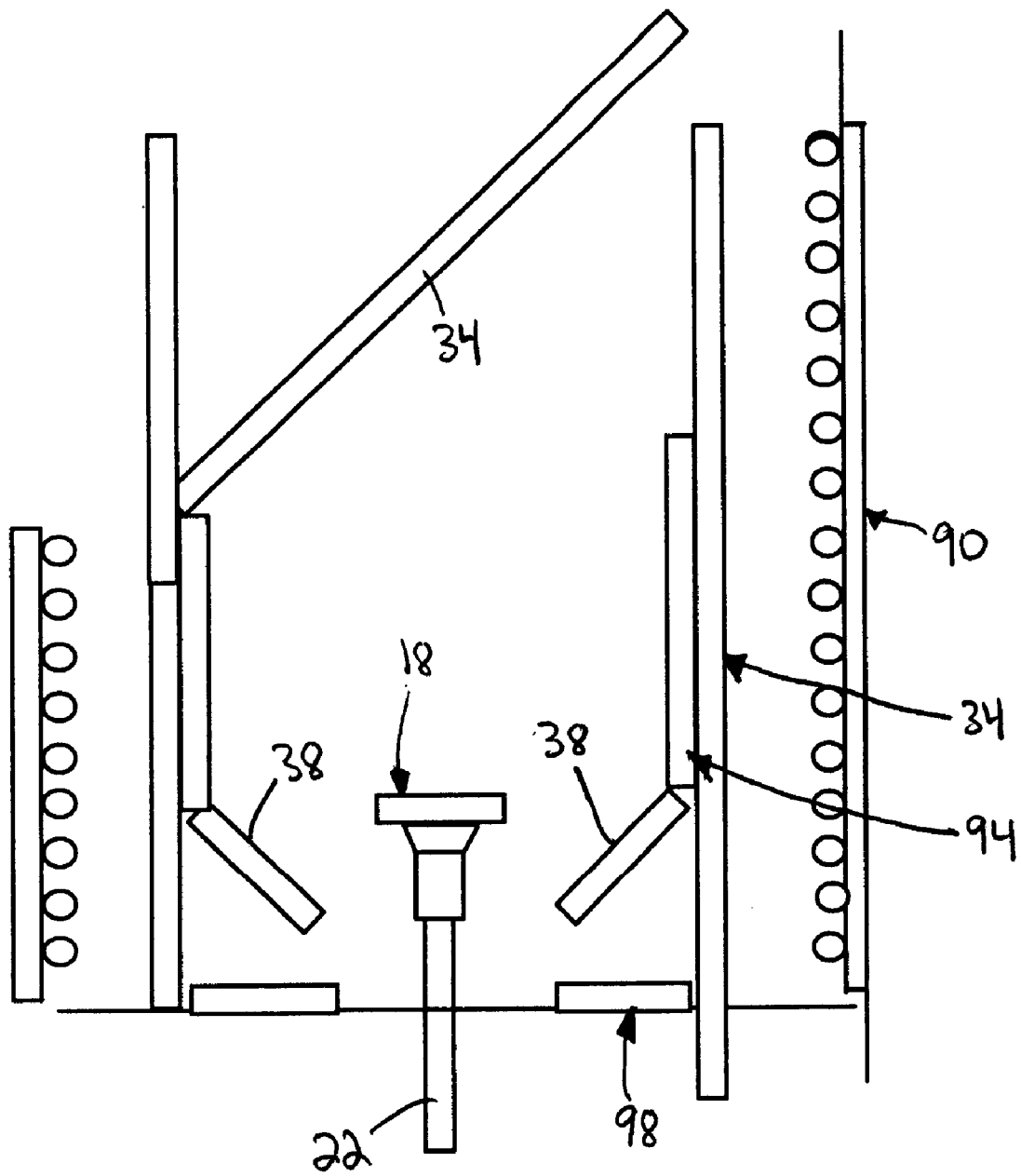
FIG. 8 is a schematic view of a machine vision system embodying the present invention.

FIG. 8 illustrates a possible lighting setup with >hemisphere (about 75% of sphere) cloudy day lighting. Parts similar to those described above are given the same reference numerals in FIG. 8. Additionally, this lighting setup includes LED boards 90, a gray filter or diffuser 94, and a black background 98. The mirrors 38 are preferably silvered mirrors if cloudy day lighting is employed, or may be replaced with beam splitters.

What is claimed is:

1. An apparatus for inspecting an LCC device, the apparatus comprising:

at least one mirror having front and rear non-parallel surfaces;

an LCC support mechanism adapted to support an LCC device in spaced relation to said at least one mirror;

a first frequency reflective coating on said front surface;

a second frequency reflective coating on said rear surface, said second frequency being different from said first frequency;

a first light source emitting light of the first frequency;

a second light source emitting light of the second frequency; and a camera positioned to view an image of the LCC device reflected off the front surface of said mirror when said first light source is lit, and reflected off the rear surface of said mirror when said second light source is lit, wherein said front and rear surfaces of said at least one mirror are angled to provide two different perspectives of a side edge of said LCC device.

2. The apparatus of claim 1, wherein said at least one mirror includes four substantially identical mirrors positioned around four sides of the LCC device.

3. The apparatus of claim 1, further comprising a white diffuser interposed between said at least one mirror and both of said first and second light sources such that light emitted from said light sources must pass through said white diffuser prior to reaching said LCC device.

4. The apparatus of claim 1, wherein said front and rear surfaces are both substantially planar.

5. The apparatus of claim 1, wherein said first and second light sources include respective first and second pluralities of light emitting diodes.

6. The apparatus of claim 1, further comprising a third light source emitting light of a third frequency different from the first and second frequencies, said third light source positioned to direct light through both the front and rear surfaces and onto the LCC device.

7. The apparatus of claim 6, wherein said third light source is angled to result in dark field illumination of the LCC device.

8. An apparatus for facilitating the inspection of an LCC device with a camera, the apparatus comprising:
   a first surface coated with a first frequency reflective coating and angled to permit the camera to view a side edge of the LCC device from a first perspective when the LCC device is illuminated with light of the first frequency; and
   a second surface coated with a second frequency reflective coating and angled to permit the camera to view a side edge of the LCC device from a second perspective, different from the first perspective, when the LCC device is illuminated with light of the second frequency;
   wherein the second frequency is different from the first frequency and the second perspective is different from the first perspective; and
   wherein the first and second surfaces are the non-parallel front and rear surfaces, respectively, of a first mirror.

9. An apparatus for facilitating the inspection of an LCC device with a camera, the apparatus comprising:
   a first surface coated with a first frequency reflective coating and angled to permit the camera to view a side edge of the LCC device from a first perspective when the LCC device is illuminated with light of the first frequency;
   a second surface coated with a second frequency reflective coating and angled to permit the camera to view a side edge of the LCC device from a second perspective, different from the first perspective, when the LCC device is illuminated with light of the second frequency;
   wherein the second frequency is different from the first frequency and the second perspective is different from the first perspective;
   wherein the first and second surfaces are the non-parallel front and rear surfaces, respectively, of a first mirror; and
   a plurality of mirrors substantially identical to the first mirror and arranged around the LCC device to provide first and second perspective views of a plurality of sides of the LCC device.

10. An apparatus for facilitating the inspection of an LCC device with a camera, the apparatus comprising:
   a first surface coated with a first frequency reflective coating and angled to permit the camera to view a side edge of the LCC device from a first perspective when the LCC device is illuminated with light of the first frequency;
   a second surface coated with a second frequency reflective coating and angled to permit the camera to view a side edge of the LCC device from a second perspective, different from the first perspective, when the LCC device is illuminated with light of the second frequency;
   wherein the second frequency is different from the first frequency and the second perspective is different from the first perspective; and
   a first plurality of LEDs selectively emitting light of the first frequency and a second plurality of LEDs selectively emitting light of the second frequency.

* * * * *